United States Patent
Kavuru et al.

(10) Patent No.: US 12,180,142 B1
(45) Date of Patent: Dec. 31, 2024

(54) SYNTHESIS PROCESS FOR HIGH PURITY ISOSULFAN BLUE USING FLASH CHROMATOGRAPHY IN COMMERCIAL PLANT SCALE

(71) Applicant: Rising Pharma Holdings, Inc., East Brunswick, NJ (US)

(72) Inventors: Vimal Kavuru, Rumson, NJ (US); Kamalkishore Pati, Morganville, NJ (US)

(73) Assignee: Rising Pharma Holdings, Inc., East Brunswick, NJ (US)

( * ) Notice: Subject to any disclaimer, the term of this patent is extended or adjusted under 35 U.S.C. 154(b) by 0 days.

(21) Appl. No.: 18/584,742

(22) Filed: Feb. 22, 2024

(51) Int. Cl.
*C07C 303/44* (2006.01)

(52) U.S. Cl.
CPC ........ *C07C 303/44* (2013.01); *C07C 2601/16* (2017.05)

(58) Field of Classification Search
CPC ............................ C07C 303/44; C07C 2601/16
See application file for complete search history.

(56) References Cited

U.S. PATENT DOCUMENTS

2019/0010330 A1* 1/2019 Vyas ...................... C01B 17/98

* cited by examiner

*Primary Examiner* — Yevgeny Valenrod
*Assistant Examiner* — Blaine G Doletski
(74) *Attorney, Agent, or Firm* — Nikitas E. Nicolakis; Lombard & Geliebter LLP

(57) ABSTRACT

A composition including a N-[4-[[4-(diethyl amino) phenyl](2,5-disulfophenyl)methylene]-2,5-cyclohexadien-1-ylidene]-N-ethylethanaminium sodium salt, where the N-4-4-(diethylamino)phenyl (2,5-disulfophenyl)methylene-2,5-cyclohexadien-1-ylidene-N-ethylethanaminium sodium salt is at least 90% of the weight of such composition. A method of making the composition by a process including sulphonating 2-chlorobenzaldehyde, treatment with sodium sulphite and subsequent basification, a condensation step, an oxidation step and a purification step comprising utilizing HPLC to monitor the sulphonating step, the treatment step, the condensation step, and/or the oxidation step, to determine when one or more reactions of such sulphonating step, treatment step, condensation step, and/or oxidation step are substantially complete and ending such one or more reactions on the basis of the HPLC monitoring. The purification step utilizes flash chromatography to obtain a high purity N-[4-[[4-(diethyl amino) phenyl](2,5-disulfophenyl)methylene]-2,5-cyclohexadien-1-ylidene]-N-ethylethanaminium sodium salt.

12 Claims, 7 Drawing Sheets

SYNTHETIC SCHEME

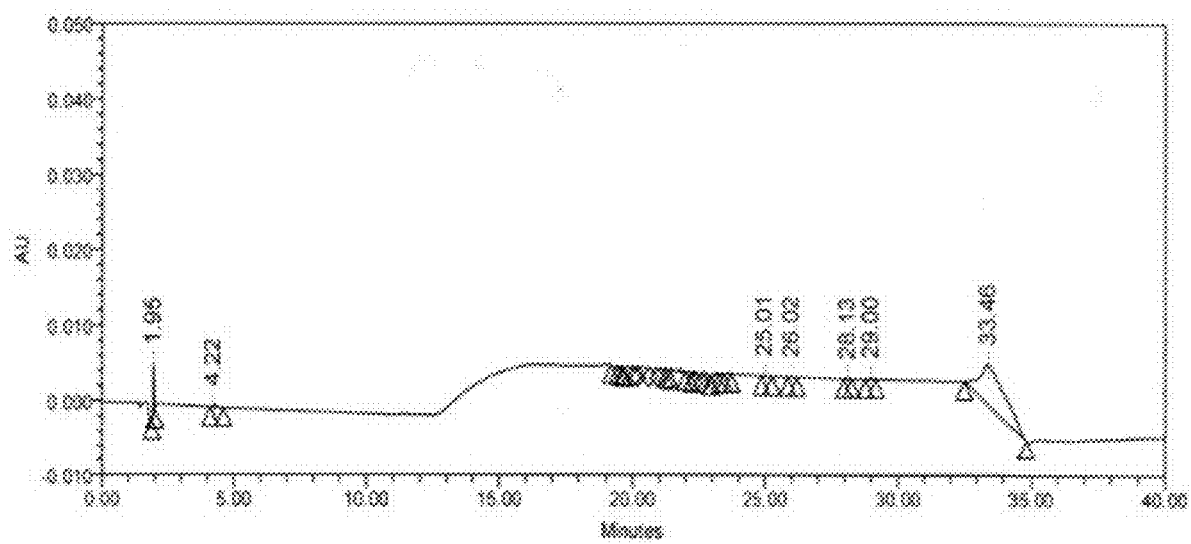
FIG. 2  Blank solution Chromatogram

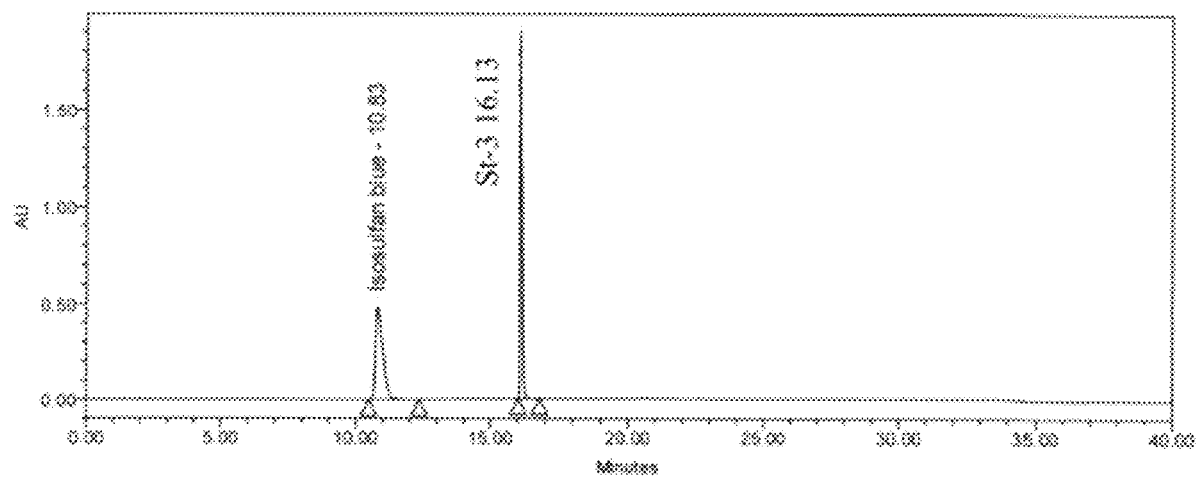
FIG. 3 A chromatogram of System suitability for ISB standard.

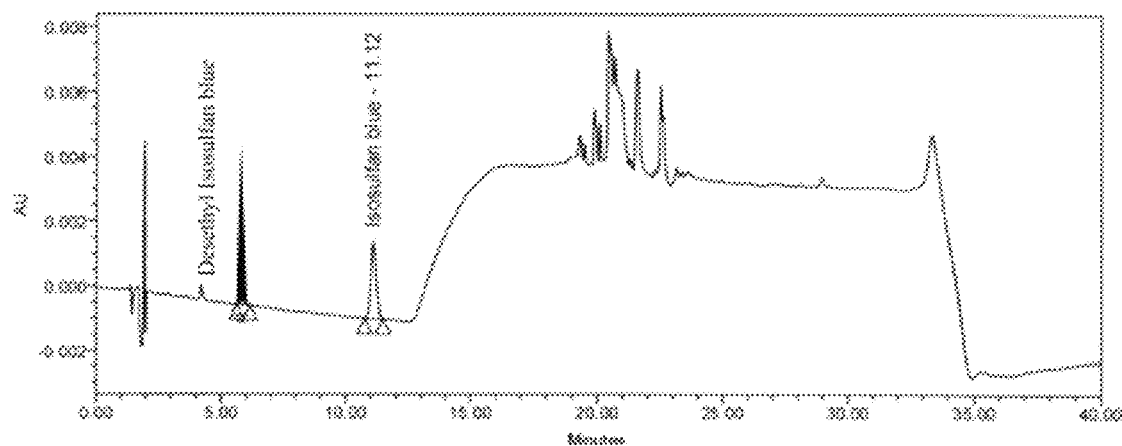
FIG. 4A LOQ Standard Chromatogram
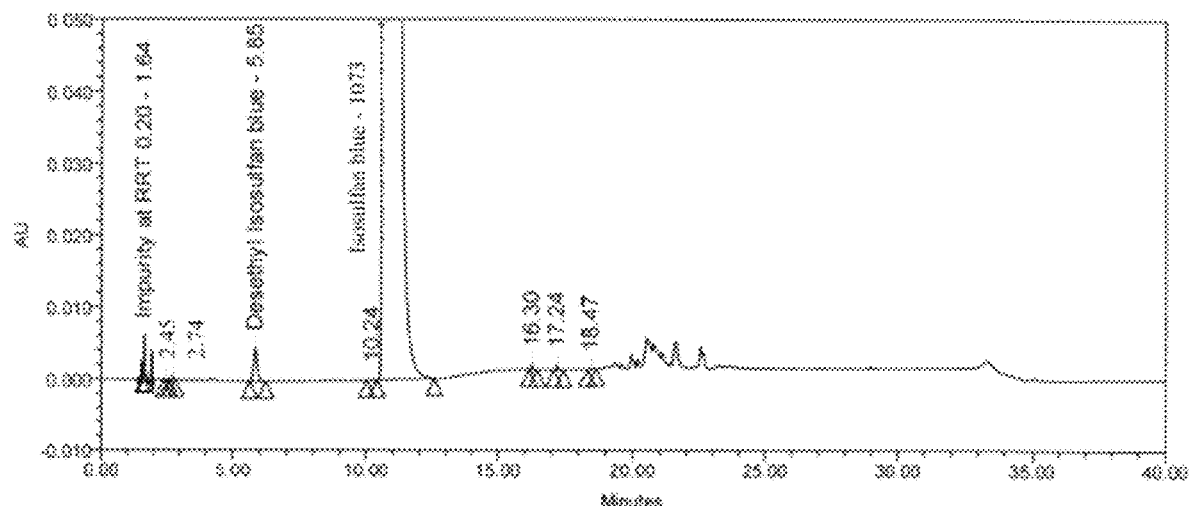
FIG. 4B Standard Sample (ISB) Chromatogram

| | SAMPLE INFORMATION | |
|---|---|---|
| SAMPLENAME: Blank | | Acquired by: sagarb |
| Vial: 1 | | Date Acquired: 27/07/2021 17:13:33 IST |
| Injection #2 | | Date Processed: 28/07/2021 17:37:57 IST |
| Injection Volume: 10.00 uL | | Acq Method Set: 7525_CP_METH |
| Run Time: 40.00 Minutes | | Processing Method: 7525_CP_Blank_Proc02 |
| Sample Set Name: 270721_7525_CP_01 | | Channel Name: W2489 ChA |
| Project Name: QC-093-JUL-21 | | Processed Channel Descr: W2489 ChA 220nm |
| Instrument ID No. QC_EQP_093 | | Processeed By: manmadharaob/Analyst |

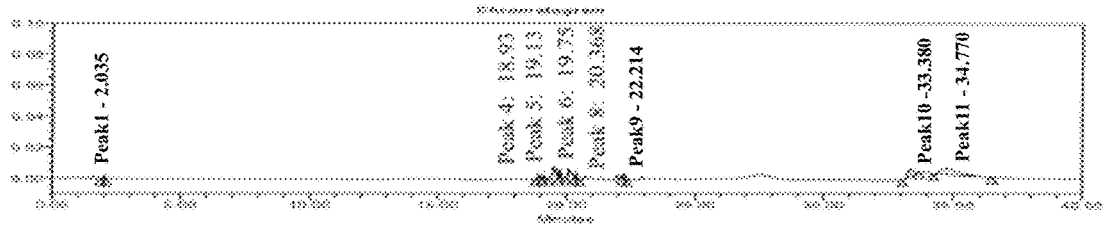

| | Peak Results | | | | |
|---|---|---|---|---|---|
| | Name | RT | Area | % Area | Height (µV) | Int Type |
| 1 | Peak1 | 2.04 | 11173 | 3.129 | 2932 | BB |
| 2 | Peak2 | 8.62 | | | | Missing |
| 3 | Peak3 | 15.78 | | | | Missing |
| 4 | Peak4 | 18.93 | 20784 | 5.82 | 2751 | BB |
| 5 | Peak5 | 19.13 | 9601 | 2.689 | 2287 | BB |
| 6 | Peak6 | 19.75 | 23499 | 6.58 | 5620 | BB |
| 7 | Peak7 | 20.11 | | | | Missing |
| 8 | Peak8 | 20.37 | 12896 | 3.611 | 3140 | BB |
| 9 | Peak9 | 22.21 | 17452 | 4.887 | 3561 | BB |
| 10 | Peak10 | 33.38 | 74501 | 20.86 | 4339 | BB |
| 11 | Peak11 | 34.77 | 187203 | 52.42 | 3955 | BB |
| Sum | | | 357109 | 100.00 | | |

| | Result Sign Off | | | |
|---|---|---|---|---|
| | Sample Name | Result Id | Sign Off Full Name | Sign Off Date |
| 1 | Blank | 4728 | Manmadha Rao B. (manmadharaob) | 28/07/2021 17:52:40 IST |
| 2 | Blank | 4728 | Srinadh R. (srinadhr) | 28/07/2021 21:02:27 IST |

| Result Sign Off |
|---|
| Sign Off Reason |
| 1 Sign Off Level 1, Reason: Data Processed and submitting for review |
| 2 Sign Off Level 2, Reason: Data review and approved |

FIG. 5 Blank Run Chromatogram of Dilutent

|  | SAMPLE INFORMATION |  |
|---|---|---|
| SAMPLENAME: S S Solution |  | Acquired by: sagarb |
| Vial: 2 |  | Date Acquired: 27/07/2021 17:54:34 IST |
| Injection # 1 |  | Date Processed: 28/07/2021 17:46:10 IST |
| Injection Volume: 10.00 uL |  | Acq Method Set: 7525_CP_METH |
| Run Time: 40.00 Minutes |  | Processing Method: 7525_CP_S S Soution_Proc01 |
| Sample Set Name: 270721_7525_CP_01 |  | Channel Name: W2489 ChA |
| Project Name: QC-093-JUL-21 |  | Processed Channel Descr: W2489 ChA 220nm |
| Instrument ID No. QC_EQP_093 |  | Processeed By: manmadharaob/Analyst |

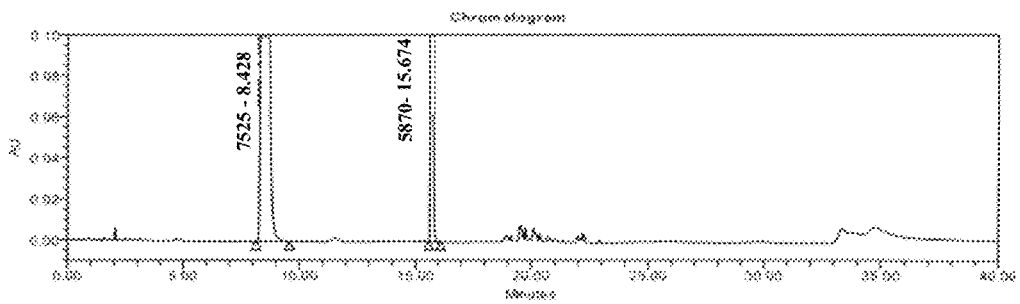

| Peak Results | | | | | | | | | |
|---|---|---|---|---|---|---|---|---|---|
|  | Name | RT | Area | % Area | Height (µV) | RT Ratio | Int Type | USP Resolution | USP Tailing | USP Plate Count |
| 1 | 7525 | 8.43 | 9518553 | 50.925 | 625279 | 1.00 | BB |  | 1.8 | 6701 |
| 2 | 5870 | 15.67 | 9172748 | 49.075 | 1756665 | 1.86 | BB | 26.19 | 1.5 | 195337 |
| Sum |  |  | 18691301 | 100.00 |  |  |  |  |  |  |

| Result Sign Off | | | |
|---|---|---|---|
|  | Sample Name | Result Id | Sign Off Full Name | Sign Off Date |
| 1 | S S Solution | 4733 | Manmadha Rao B. (manmadharaob) | 28/07/2021 17:52:42 IST |
| 2 | S S Solution | 4733 | Srinadh R. (srinadhr) | 28/07/2021 21:02:51 IST |

| Result Sign Off |
|---|
| Sign Off Reason |
| 1 | Sign Off Level 1, Reason: Data Processed and submitting for review |
| 2 | Sign Off Level 2, Reason: Data review and approved |

FIG. 6 Working standard Chromatogram

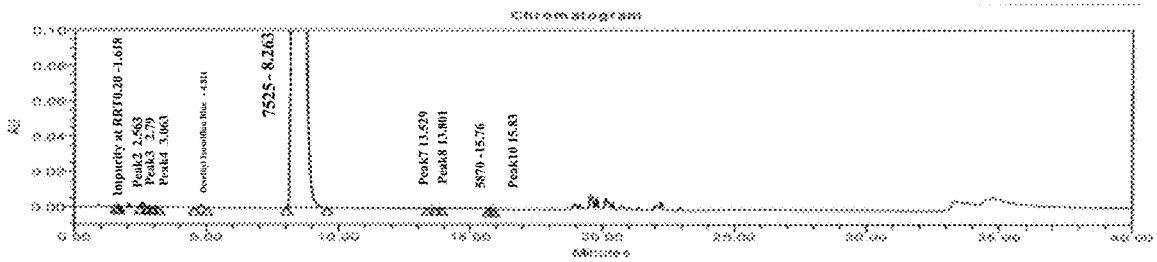

| | SAMPLE INFORMATION | |
|---|---|---|
| SAMPLENAME: 7525/21/3008 | | Acquired by: sagarb |
| Vial: 4 | | Date Acquired: 27/07/2021 22:41:27 IST |
| Injection #1 | | Date Processed: 28/07/2021 17:51:38 IST |
| Injection Volume: 10.00 uL | | Acq Method Set: 7525_CP_METH |
| Run Time: 40.00 Minutes | | Processing Method: 7525_CP_CP_Sample_Proc02 |
| Sample Set Name: 270721_7525_CP_01 | | Channel Name: W2489 ChA |
| Project Name: QC-093-JUL-21 | | Processed Channel Descr: W2489 ChA 220nm |
| Instrument ID No. QC_EQP_093 | | Processeed By: manmadharaob/Analyst |

| | Peak Results | | | | | |
|---|---|---|---|---|---|---|
| | Name | RT | Area | % Area | Height (µV) | RT Ratio | Int Type |
| 1 | Impurity at RRT0.20 | 1.62 | 2404 | 0.009 | 900 | 0.20 | BB |
| 2 | Peak2 | 2.55 | 23369 | 0.089 | 5044 | 0.31 | BB |
| 3 | Peak3 | 2.79 | 1028 | 0.004 | 225 | 0.34 | BB |
| 4 | Peak4 | 3.06 | 2906 | 0.011 | 562 | 0.37 | BB |
| 5 | Desthyl Isosulfan blue | 4.81 | 11430 | 0.043 | 1397 | 0.58 | BB |
| 6 | 7525 | 8.26 | 26320965 | 99.82 | 1280693 | 1.00 | BB |
| 7 | Peak7 | 13.53 | 2246 | 0.009 | 244 | 1.64 | BB |
| 8 | Peak8 | 13.8 | 619 | 0.002 | 98 | 1.67 | BB |
| 9 | 5870 | 15.76 | 2786 | 0.011 | 759 | 1.91 | BS |
| 10 | Peak10 | 15.83 | 984 | 0.004 | 282 | 1.92 | SB |
| Sum | | | 26368737 | 100.00 | | | |

| | Result Sign Off | | | |
|---|---|---|---|---|
| | Sample Name | Result Id | Sign Off Full Name | Sign Off Date |
| 1 | 7525/21/3008 | 4761 | Manmadha Rao B. (manmadharaob) | 28/07/2021 17:52:55 IST |
| 2 | 7525/21/3008 | 4761 | Srinadh R. (srinadhr) | 28/07/2021 21:05:54 IST |

| | Result Sign Off |
|---|---|
| | Sign Off Reason |
| 1 | Sign Off Level 1, Reason: Data Processed and submitting for review |
| 2 | Sign Off Level 2, Reason: Data review and approved |

FIG. 7 ISB (Lot 3003) test sample Chromatogram

SYNTHESIS PROCESS FOR HIGH PURITY ISOSULFAN BLUE USING FLASH CHROMATOGRAPHY IN COMMERCIAL PLANT SCALE

FIELD OF THE INVENTION

The present application relates to improved synthesis and purification processes for the commercial production of Isosulfan blue.

BACKGROUND OF INVENTION

Isosulfan blue (CAS Number 68238-36-8) is chemically known as N-[4-[[4-(diethyl amino) phenyl](2,5-disulfophenyl)methylene]-2,5-cyclohexadien-1-ylidene]-N-ethyl-ethanaminium sodium salt and is represented by Formula I as shown below.

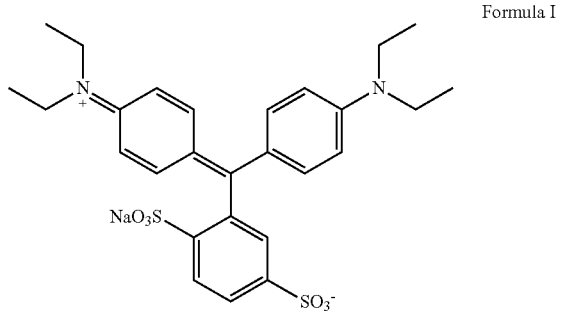

Formula I

This molecule is a triarylmethane dye. Isosulfan blue is sold under the brand name Lymphazurin, and used as a contrast agent for delineation of lymphatic vessels via a procedure called lymphography and is particularly useful as a cancer diagnostic agent. Isosulfan blue is available as 1% (10 mg/ml) 5 ml solution for injection.

Based on published literature data, in several US patents (U.S. Pat. No. 1,531,507 (the "'507 patent"), U.S. Pat. No. 7,534,911 (the "'911 patent"), U.S. Pat. No. 8,969,616 (the "'616 patent")) and WO2017118882 (the "'882 publication"), numerous processes have been reported for the synthesis of dyes including Isosulfan blue. Common synthesis of Isosulfan blue was first reported in the '507 patent. In this patent, Isosulfan blue is made by converting Ortho chlorobenzaldehyde to sodium salt of 2-chlorobenzaldehyde-5-sulfonic acid by sulphating using oleum (26% to 65%) and sodium carbonate, followed by treatment with sodium sulphite to obtain benzaldehyde-2,5-disulfonic acid sodium salt followed by condensation with alkyl aryl amine to produce isoleuco acid. The acid was oxidized to yield Isosulfan blue, but the purity and yield was not reported. Initially the Tri-Aryl N-Alkyl dyes (molecules) thus prepared are used mainly for dyeing fabric, paper colouring agents, and printing inks.

The '911 patent reported an alternate route of synthesis for Isosulfan blue, disclosing sulphonating Ortho chlorobenzaldehyde with Oleum (23%-65%) to attain 2-chlorobenzaldehyde-5-sulfonic acid, which is then reacted with sodium sulphite and followed by basification to produce sodium salt of benzaldehyde-2,5-disulfonic acid. This sodium salt of benzaldehyde-2,5-disulfonic acid is then treated with sodium sulphite to acquire disodium salt which is then subject to condensation with diethyl aniline to yield 2-(bis(4-(diethylamino) phenyl) methyl)benzene-1,4-disulfonate sodium upon oxidation, followed by treatment of the reaction mass with ammonium dichromate in presence of sulfuric acid to result in Isosulfan blue.

The '616 patent discusses another synthesis route for Isosulfan blue. In this route, 4-Chloro-3-formylbenzenesulfonic acid is reacted with sodium sulphite and sodium sulphite mixture in water at very high temperature, above 150° C., and under high pressure using Methanol and (dimethylformamide) DMF and Dichloromethane solvents for purification of crude compound with poor yield to get Sodium-2-formylbenzene-1,4-disulfonate. The next step is the reaction of Sodium-2-formylbenzene-1,4-disulfonate with NN-Diethyl aniline, in the presence of urea and acetic acid at reflux for a day, then separated by cooling the reaction mixture and adding Methanol to derive crude 2-(Bis(4-(diethylamino)phenyl) methyl)benzene-1,4-disulfonic acid. The crude material upon purification results in 2-(Bis(4-(diethylamino)phenyl)methyl)benzene-1,4-disulfonicacid, which is oxidized in the presence of silver oxide in methanol media, and further isolated using Diisopropylether to obtain Isosulfan blue. This process is very complex, but still there is desethyl isosulfan blue impurity in the final active pharmaceutical ingredient (API).

Hence, there is a need for improved processes for preparing Isosulfan blue which are suitable for large scale production, and produce high yield and/or high purity.

SUMMARY OF THE INVENTION

The present invention is directed to improved processes for producing Isosulfan blue that are significant improvements over prior processes. In at least one embodiment, the processes address the objective of producing Isosulfan blue in commercial scale with high purity, that is, having less than 0.1% of desethyl isosulfan blue impurity. In this regard, the processes provide simple, and commercially scalable, safe, and cost effective options for the preparation of Isosulfan blue.

The present application further provides improved purification processes for the preparation of Isosulfan blue, where one or more of the drawbacks of the prior processes mentioned above are overcome by the novel use of flash chromatography.

In accordance therewith, the purification process provides a product within the limits of pharmaceutically acceptable known and unknown impurities, i.e., known impurities below 0.5% and any unknown impurities below 0.1%.

According to an embodiment, there is provided a purification process that incorporates flash chromatography techniques for the preparation of Isosulfan blue, the process including the following steps:

Sulphonating 2-chlorobenzaldehyde with a sulphonating agent to obtain 4-Chloro-3-formyl-benzenesulfonic acid;

Treating 4-Chloro-3-formyl-benzenesulfonic acid with sodium sulphite and subsequent basification thereof to obtain Benzaldehyde-2,5-disulfonic acid sodium salt.

Condensation of Benzaldehyde-2,5-disulfonic acid sodium salt with N,N-diethylaniline, using acetic acid or hydrochloric acid to obtain 2-(Bis(4-diethylamino) phenyl)methyl) benzene-1,4-disulfonic acid disodium salt;

Oxidation of 2-(Bis(4-diethylamino)phenyl)methyl) benzene-1,4-disulfonic acid disodium salt with an oxidizing agent using an acid and solvent to obtain Isosulfan blue crude; and Purifying the Isosulfan blue crude using flash chromatography techniques to obtain pure Isosulfan blue, i.e., at least 90% Isosulfan blue, as discussed herein.

In an embodiment, the present invention is directed to a composition including N-[4-[[4-(diethyl amino) phenyl](2,5-disulfophenyl)methylene]-2,5-cyclohexadien-1-ylidene]-N-ethylethanaminium sodium salt, where the N-[4-[[4-(diethyl amino) phenyl](2,5-disulfophenyl)methylene]-2,5-cyclohexadien-1-ylidene]-N-ethylethanaminium sodium salt is at least 90% of the weight of such composition. Preferably, the N-[4-[[4-(diethyl amino) phenyl](2,5-disulfophenyl)methylene]-2,5-cyclohexadien-1-ylidene]-N-ethylethanaminium sodium salt is 90% to 99.9% of the weight of such composition, and any range within this range. Even more preferably, the N-[4-[[4-(diethyl amino) phenyl](2,5-disulfophenyl)methylene]-2,5-cyclohexadien-1-ylidene]-N-ethylethanaminium sodium salt is 99.0% to 99.9% of the weight of such composition. In yet another embodiment, the composition includes a desethyl isosulfan blue (also referred to as desethyl ISB) impurity, and a chemical structure of such desethyl ISB impurity is 3-((4-(Diethyliminio)cyclohexa-2,5-dien-1-ylidene)(4-(ethylamino)phenyl)methyl)-4-sulfobenzenesulfonate. An amount of desethyl ISB impurity is preferably below 0.07% by weight, and such desethyl ISB impurity can be 0.020% to 0.07% by weight, such as 0.03% and 0.07% by weight, or any range within these ranges. In another aspect of the invention, the composition including N-[4-[[4-(diethyl amino) phenyl](2,5-disulfophenyl)methylene]-2,5-cyclohexadien-1-ylidene]-N-ethylethanaminium sodium salt includes 2-(Bis(4-diethylamino)phenyl)methyl)benzene-1,4-disulfonic acid disodium salt, where such 2-(Bis(4-diethylamino) phenyl)methyl)benzene-1,4-disulfonic acid disodium salt is not more than 0.1% of the weight of the composition, such as 0.01 to 0.05% or any range within this range.

In yet another aspect of the invention, the composition including N-[4-[[4-(diethyl amino) phenyl](2,5-disulfophenyl)methylene]-2,5-cyclohexadien-1-ylidene]-N-ethylethanaminium sodium salt includes one or more of the following impurities: arsenic, lead, mercury, cadmium, cobalt, vanadium, and nickel, where an amount of arsenic is by weight below 0.030 ppm (e.g., 0.001 to 0.02 ppm), an amount of lead is by weight below 0.110 ppm (e.g., 0.01 to 0.05 ppm), an amount of mercury is by weight below 0.03 ppm (e.g., 0.001 to 0.02 ppm), an amount of cadmium is by weight below 0.030 ppm (e.g., 0.001 to 0.02 ppm), an amount of cobalt is by weight below 0.015 ppm (e.g., 0.0001 to 0.0 ppm), an amount of vanadium is by weight below 0.030 ppm (e.g., 0.001 to 0.02 ppm), and an amount of nickel is by weight below 0.300 ppm (e.g., 0.001 to 0.02 ppm). All subranges within the identified ranges are envisioned in this patent application.

In a further aspect of the invention, the composition including N-[4-[[4-(diethyl amino) phenyl](2,5-disulfophenyl)methylene]-2,5-cyclohexadien-1-ylidene]-N-ethylethanaminium sodium salt includes a chromium impurity which is not more than 1.3 ppm by weight of the composition, such as 0.1 to 1 ppm, or any range within this range.

In another embodiment, the present invention is directed to a substantially pure N-[4-[[4-(diethyl amino) phenyl](2,5-disulfophenyl)methylene]-2,5-cyclohexadien-1-ylidene]-N-ethylethanaminium sodium salt made by a process including the steps of:

- a sulphonating step including sulphonating 2-chlorobenzaldehyde with a sulphonating agent to obtain 4-chloro-3-formyl sulphonic acid;
- a treatment step including treating 4-chloro-3-formyl sulphonic acid with sodium sulphite and subsequent basification thereof to obtain 1-formylbenzene-2,5-sulphonic acid disodium salt;
- a condensation step including condensation reacting of 1-formyl benzene-2,5-sulphonic acid disodium salt with N,N-diethylaniline using a first acid to obtain a 4-[Bis[4-diethylamino)phenyl]methyl]benzene-2,5-disulphonic acid disodium salt;
- an oxidation step including oxidation reacting of 4-[bis[4-(diethylamino)phenyl]methyl]benzene-2,5-disulphonic acid with an oxidizing agent, using a second acid and a solvent, to obtain N-4-4-(diethylamino) phenyl (2,5-disulfophenyl)methylene-2,5-cyclohexadien-1-ylidene-N-ethylethanaminium sodium salt;
- a purification step including purification of N-4-4-(diethylamino)phenyl (2,5-disulfophenyl)methylene-2,5-cyclohexadien-1-ylidene-N-ethylethanaminium sodium salt; and
- utilizing HPLC to monitor the sulphonating step, the treatment step, the condensation step, and/or the oxidation step, to determine when one or more reactions of such sulphonating step, treatment step, condensation step, and/or oxidation step are substantially complete and ending such one or more reactions on the basis of the HPLC monitoring.

In another embodiment, the sulphonating agent in the sulphonating step includes oleum, and the basification of the treatment step includes the use of NaOH solution. In an aspect of the invention, the first acid in the condensation step is acetic acid or hydrochloric acid. In yet another aspect, the second acid and the solvent of the oxidation step are sulfuric acid and methanol, respectively.

In yet another embodiment, the sulphonating agent in the sulphonating step includes oleum having a concentration of 15-30% by weight. In another aspect, the basification of the treatment step includes adjusting the pH from 2-3 to 10-11.5, such as from 2.5 to 11. In yet another aspect, treatment step further includes isolation to obtain solid 1-formyl benzene-2,5-sulphonic acid disodium salt. Also, the condensation step further includes adjusting the pH to 10.5 to 11.5 with sodium hydroxide in the presence of methanol and isolating the product. In an embodiment, the oxidation step is carried out at −10 to −4 degrees Celsius, and the N-4-4-(diethylamino)phenyl (2,5-disulfophenyl)methylene-2,5-cyclohexadien-1-ylidene-N-ethylethanaminium sodium salt is then isolated.

In the present disclosure, the term "isolated" or "isolation" is used to refer to the separation of the product from the reaction mixture. Such separation can be done via different methods, such as one or a combination of the following: Precipitation, filtration, washing, separation from water or from organic solvent, crystallization, distillation of solvent (e.g., organic solvent) from the reaction mixture or from column fractions. For example, the term "isolated" can mean precipitation and/or filtering and/or washing.

Preferably, the purification step includes the use of flash chromatography. More preferably, the purification step includes the use of flash chromatography with 5-10% of methanol in a methylene chloride mixture as eluent, and where the purification step further includes mixing fractions from the flash chromatography, and distilling solvent to obtain the substantially pure N-4-4-(diethylamino)phenyl (2,5-disulfophenyl)methylene-2,5-cyclohexadien-1-ylidene-N-ethylethanaminium sodium salt.

HPLC may be used to monitor the sulphonating step, the treatment step, the condensation step, and the oxidation step to determine when one or more reactions of such sulphonating step, treatment step, condensation step, and oxidation step are substantially complete and ending such one or more reactions on the basis of the HPLC monitoring.

In a further aspect, the present invention is directed to a method of making a substantially pure N-4-4-(diethylamino) phenyl (2,5-disulfophenyl)methylene-2,5-cyclohexadien-1-ylidene-N-ethylethanaminium sodium salt including the steps of:
- a sulphonating step including sulphonating orthochlorobenzaldehyde with a sulphonating agent to obtain 4-chloro-3-formyl sulphonic acid;
- a treatment step including treating 4-chloro-3-formyl sulphonic acid with sodium sulphite and subsequent pH adjustment thereof to obtain 1-formyl benzene-2,5-sulphonic acid disodium salt; a condensation step including condensation reacting of 1-formyl benzene-2,5-sulphonic acid disodium salt with N,N-diethylaniline using a first acid to obtain a 4-[Bis[4-diethylamino) phenyl]methyl]benzene-2,5-disulphonic acid disodium salt;
- an oxidation step including oxidation reacting of 4-[bis [4-(diethylamino)phenyl]methyl]benzene-2,5-disulphonic acid with an oxidizing agent, using a second acid and a solvent, to obtain N-4-4-(diethylamino) phenyl (2,5-disulfophenyl)methylene-2,5-cyclohexadien-1-ylidene-N-ethylethanaminium sodium salt;
- a purification step including purification of N-4-4-(diethylamino)phenyl (2,5-disulfophenyl)methylene-2,5-cyclohexadien-1-ylidene-N-ethylethanaminium sodium salt; and utilizing HPLC to monitor the sulphonating step, the treatment step, the condensation step, and/or the oxidation step, to determine when one or more reactions of such sulphonating step, treatment step, condensation step, and/or oxidation step are substantially complete and ending such one or more reactions on the basis of the HPLC monitoring.

In a further aspect of the invention, the sulphonating agent in the sulphonating step includes oleum. In an aspect of the invention, the pH adjustment of the treatment step includes the use of a base. In another aspect of the invention, the first acid in the condensation step includes acetic acid or hydrochloric acid. In yet another aspect of the invention, the second acid and the solvent of the oxidation step include sulfuric acid and methanol, respectively.

In an embodiment, the sulphonating agent in the sulphonating step includes oleum having a concentration of 15-30%. In another embodiment, the pH adjustment step includes adjusting the pH from 2-3 to 10-11.5, such as from 2.5 to 11. In yet another embodiment, the treatment step includes isolation by filtration to obtain solid 1-formyl benzene-2,5-sulphonic acid disodium salt. In another aspect of the invention, the condensation step includes adjusting the pH to 10.5 to 11.5 with base in the presence of methanol to precipitate from the reaction mixture, the precipitate is then isolated and washed using isopropyl alcohol. In yet another aspect of the invention, the oxidation step is be carried out at −10 to −4 degrees Celsius, and the N-4-4-(diethylamino)phenyl (2,5-disulfophenyl)methylene-2,5-cyclohexadien-1-ylidene-N-ethylethanaminium sodium salt is then isolated.

Preferably, the purification step includes the use of chromatography. More preferably, the purification step includes the use chromatography and a flash column packed with silica gel and solvent, where the N-4-4-(diethylamino)phenyl (2,5-disulfophenyl)methylene-2,5-cyclohexadien-1-ylidene-N-ethylethanaminium sodium salt moves at a different speed from impurities, resulting in a higher purity N-4-4-(diethylamino)phenyl (2,5-disulfophenyl)methylene-2,5-cyclohexadien-1-ylidene-N-ethylethanaminium sodium salt fractions.

In an embodiment, the purification step includes the use of flash chromatography with 5-10% of methanol in a methylene chloride mixture. In another embodiment, the purification step further includes mixing fractions from the flash chromatography, and distilling solvent to obtain the substantially pure N-4-4-(diethylamino)phenyl (2,5-disulfophenyl)methylene-2,5-cyclohexadien-1-ylidene-N-ethylethanaminium sodium salt.

In an aspect of the invention, the purification step includes: purification of N-4-4-(diethylamino)phenyl (2,5-disulfophenyl)methylene-2,5-cyclohexadien-1-ylidene-N-ethylethanaminium sodium salt by absorption over silica gel (60-120 mesh) in a column, where solvents used in the column comprise methanol, dichloromethane and/or 5-10% methanol in dichloromethane as eluent, and the solvent feed is subject to 35-40 psi nitrogen pressure, and collected fractions are analysed using HPLC, and fractions having purity >99.8% purity of N-4-4-(diethylamino)phenyl (2,5-disulfophenyl)methylene-2,5-cyclohexadien-1-ylidene-N-ethylethanaminium sodium salt are combined and concentrated to obtain a more purified N-4-4-(diethylamino)phenyl (2,5-disulfophenyl)methylene-2,5-cyclohexadien-1-ylidene-N-ethylethanaminium sodium salt.

BRIEF DESCRIPTION OF THE DRAWINGS

FIG. 2 is a chromatogram showing a blank solution.

FIG. 3 is a chromatogram showing System suitability for ISB standard.

FIG. 4A is a LOQ Standard Chromatogram.

FIG. 4B is a chromatogram showing a Standard Sample (ISB).

FIG. 5 shows a chromatogram of diluent.

FIG. 6 shows a chromatogram of a working standard.

FIG. 7. Shows a chromatogram of an actual sample of the present invention.

DETAILED DESCRIPTION

Figure 1:
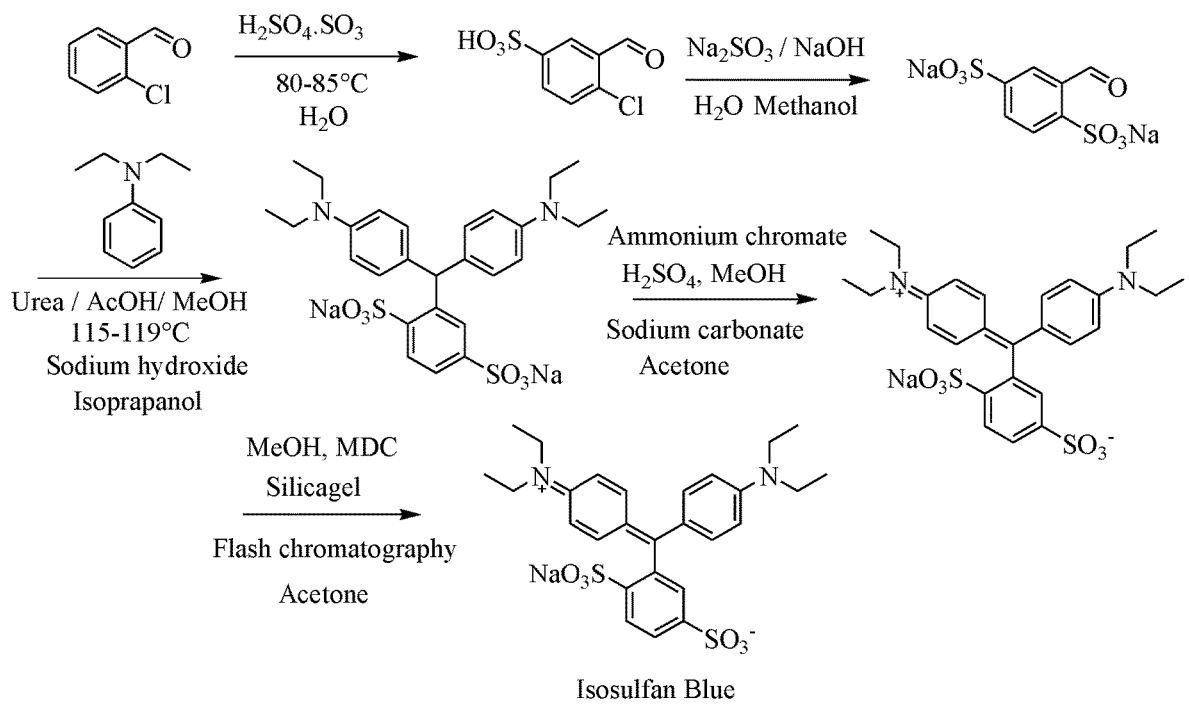
FIG. 1 is a diagram showing the synthetic schema for producing Isosulfan blue according to an embodiment.

The present application generally provides processes for generating Isosulfan blue ("ISB") within the pharmaceutical acceptable limits of desethyl isosulfan blue and other impurities, as discussed herein.

One of the issues resolved by the present invention is that, previously, an undesirable amount of desethyl isosulfan blue impurity was typically formed due to the use of oxidizing agents in the formation of ISB, which impurity was difficult to remove even after several purification steps. In the present application, each of the reactions steps is performed to substantial completion, as determined by the analytical methods discussed herein, followed by the use flash chromatography to reduce the desethyl ISB or other impurity to within pharmaceutically acceptable or desirable limits. It was further found that the techniques disclosed herein for reducing impurity are commercially viable, reproducible to provide quality end products, and/or results in time savings.

In some aspects of the invention, a process for the preparation of N-4-4-(diethylamino)phenyl (2,5-disulfophenyl)methylene-2,5-cyclohexadien-1-ylidene-N-ethylethanaminium, Sodium salt includes combining flash chromatographic purification process.

In other aspects of the invention, the process includes the following steps: (a) Reacting 2-chlorobenzaldehyde with a sulfonating agent to obtain 4-chloro-3-formyl Sulphonic acid; (b) treating 4-chloro-3-formylsulphonic acid with sodium sulphite and subsequent basification thereof to obtain 1-formyl benzene-2,5-Sulphonic acid disodium salt; (d) condensation of 1-formyl benzene-2,5-Sulphonic acid disodium salt with N,N-diethylaniline using hydrochloric acid or acetic acid to obtain a 4-[Bis[4-diethylamino)phenyl]methyl]benzene-2,5-disulphonic acid disodium salt; (d) oxidation of 4-[Bis[4-diethylamino)phenyl]methyl]benzene-2,5-disulphonic acid disodium salt with an oxidizing agent, using an acid and a solvent, to yield crude Isosulphan Blue which is purified using flash chromatographic technology to obtain high pure (99.5% or purer) Isosulfan blue with less than 0.1% of desethyl ISB impurity.

In an embodiment, the present invention is directed to a process of purifying Isosulfan blue using Flash chromatography as mentioned to obtain at least 99.5% purity.

In another embodiment, a process purifying Isosulfan blue using Flash chromatography results in desethyl ISB impurity level below 0.1%.

In an embodiment of the invention, in step (a) above, the sulfonating agent is oleum having a concentration in a range of 20 to 70% by weight. In another embodiment, the condensation (step (c) above) is be carried out at temperature in the range of 80-110° C. The condensation is carried out for 6 to 20 hours. In yet another embodiment, the 4-[Bis[4-diethylamino)phenyl]methyl]benzene-2,5-disulphonic acid disodium salt (from step (c)) is isolated at a pH range of 9 to 13. In an aspect of the invention, the oxidizing agent in step (d) is ammonium dichromate. In another aspect of the invention, the acid (in step (d)) is sulphuric acid in a concentration range of 20 to 60%.

FIG. 1 shows a reaction scheme according to the present invention. Referring to FIG. 1, the process begins with the sulfonation of 2-chlorobenzaldehyde using ~23% Oleum at 80° C.-85° C. for a sufficient period, preferably for at least 20 minutes, or more preferably for at least 30 minutes, followed by quenching the reaction mass with purified water (optionally with organic solvents mixed with the purified water) between 0° C. to 5° C. The reaction is preferably performed to at least substantial completion, e.g., at least 97 to 99% conversion of the starting material, as determined by monitoring the reaction using High-performance liquid chromatography ("HPLC"). The resulting reaction mass is then filtered therefrom, preferably under nitrogen rich atmosphere and cooled to a temperature in the range of –8° C. to –12° C., to obtain wet material of 4-Chloro-3-formylbenzenesulfonic acid.

Thereafter, the wet 4-Chloro-3-formylbenzenesulfonic acid is reacted with sodium sulphite in presence of aqueous sodium hydroxide, at a temperature in the range of 95 C to 107° C., or preferably between 100° C. to 102° C., for a period of at least 10 hours, or preferably at least 12 hours. This results in a sodium sulfonate salt such as Benzaldehyde-2, 5-disulfonic acid, sodium salt. In an embodiment, the reaction progress is monitored by HPLC and is preferably continued until achieving substantial complete, e.g., above 95% conversion of starting material, i.e., the 4-Chloro-3-formylbenzenesulfonic acid. Subsequently, the resultant product is isolated by precipitation with methanol and filtration to obtain Benzaldehyde-2, 5-disulfonic acid, sodium salt.

The Benzaldehyde-2, 5-disulfonic acid, sodium salt, is converted by mixing with N,N-Diethylaniline in the presence of urea and acetic acid or hydrochloric acid at a temperature in the range of 100° C. to 135° C., or preferably in the range of 115° C. to 119° C. for a period of at least 20 hours, and preferably at least 25 hours. In an embodiment, the reaction progress is monitored by using HPLC until there is a 98% or more conversion of the starting material, i.e., the Benzaldehyde-2, 5-disulfonic acid, sodium salt, to obtain leuco acid intermediate which is 2-(Bis(4-diethylamino)phenyl)methyl) benzene-1,4-disulfonic acid. The leuco acid intermediate is then basified with aqueous sodium hydroxide in the presence of methanol, followed by distilling off the methanol solvent from the reaction mixture and washing with isopropyl alcohol to obtain 2-(Bis(4-diethylamino)phenyl)methyl) benzene-1,4-disulfonic acid disodium salt (leuco base).

The process then proceeds to oxidation of the resulting 2-(Bis(4-diethylamino)phenyl)methyl) benzene-1,4-disulfonic acid disodium salt (leuco base) by using chromium and more specifically ammonium dichromate as the oxidation agent in presence of diluted sulfuric acid and methanol at a temperature in the range –10° C. to –4° C. for a period of 2.0 hours to 3.0 hours. In an embodiment, the reaction/oxidation progress is monitored by HPLC, until substantial completion of the oxidation reaction, i.e., at least 98% of the staring material (2-(Bis(4-diethylamino)phenyl)methyl) benzene-1,4-disulfonic acid disodium salt (leuco base)) is converted to isosulfan blue, followed by neutralizing of the converted material with sodium carbonate. This results in ISB and such ISB is isolated to obtain Isosulfan blue crude.

The Isosulfan blue crude product is further purified by using flash chromatography using methylene chloride and methanol mixture as mobile phase. The fractions are then concentrated to obtain pure Isosulfan blue, i.e., at least 90% pure ISB, preferably with less than 0.1% of desethyl isosulfan blue impurity.

In an embodiment, the present invention is directed to 4 synthesis steps, 1 purification step, and 1 analysis step. Although ISB has been synthesize before, the present invention results in very pure ISB. The use of flash chromatography in combination with other methods to prepare ISB would not be as helpful and would not get the same benefits as in the present invention since the yield would be lower.

In an aspect of the present invention, the purity of Isosulfan blue is 99.0% to 99.9% and more preferably, it is above 99.5%. In yet another aspect, the impurity of desethyl ISB is less than 0.1% by weight, preferably, it is less than 0.07%, such as between 0.03% and 0.07%. More preferably, the amount of desethyl isosulfan blue impurity is not more than 0.05%, such as between 0.01% and 0.04% or any range within this range. Further, it is preferred that the combination of all impurities is not more than 0.5%.

In another aspect, the present invention results in a composition containing Isosulfan blue in which composition has not more than 0.1% of 2-(Bis(4-diethylamino)phenyl)methyl)benzene-1,4-disulfonic acid disodium salt.

In another aspect, the basification of the treatment step (the treatment of 4-chloro-3-formyl sulphonic acid) comprises the use of base, such as NaOH solution. In yet another aspect, the first acid in the condensation step (e.g., condensation of 1-formyl benzene-2,5-sulphonic acid disodium salt) includes acetic acid or hydrochloric acid. In a further aspect, the acid and the solvent of the oxidation step (e.g., oxidation of 4-[bis[4-(diethylamino)phenyl]methyl]benzene-2,5-disulphonic acid) include sulfuric acid and methanol, respectively.

In an embodiment, the condensation step (e.g., condensation of 1-formyl benzene-2,5-sulphonic acid disodium salt) includes adjusting the pH to 10.5 to 11.5 with base, such as sodium hydroxide, in the presence of methanol and then the product is isolated.

In another embodiment, the oxidation (e.g., oxidation of 4-[bis[4-(diethylamino)phenyl]methyl]benzene-2,5-disulphonic acid) step is carried out at −10 to −4 degrees Celsius, and the N-[4-[[4-(diethyl amino) phenyl](2,5-disulfophenyl)methylene]-2,5-cyclohexadien-1-ylidene]-N-ethyl-ethanaminium sodium salt is isolated by filtration.

In yet another embodiment, the purification step (e.g., purifying N-[4-[[4-(diethyl amino) phenyl](2,5-disulfophenyl)methylene]-2,5-cyclohexadien-1-ylidene]-N-ethyl-ethanaminium sodium salt) utilizes chromatography and a column for chromatography. In an aspect of the invention, the stationary phase is silica gel and the eluent is solvent. The silica gel and solvent are loaded into a column prior to the purification of the N-[4-[[4-(diethyl amino) phenyl](2,5-disulfophenyl)methylene]-2,5-cyclohexadien-1-ylidene]-N-ethylethanaminium sodium salt.

Various steps of the present invention are described in more detail below.

The following specific examples are presented to show embodiments of carrying out the process of the present invention.

Example-1

Synthesis of 4-Chloro-3-formyl-benzenesulfonic Acid

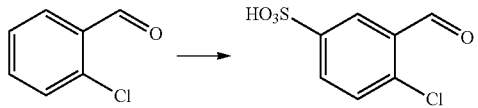 [SMILES: O=Cc1ccccc1Cl ; O=Cc1cc(S(=O)(=O)O)ccc1Cl]

2-chlorobenzaldehyde (100 g, 0.71 moles, 1.0 eq) was added to Oleum (600 g (~23%), 0.77 mole, 1.08 eq) at 0-5° C. over a period of 2-3 hrs to obtain a reaction mass. The reaction mass was then heated, and the temperature maintained for sufficient time for substantial completion of the reaction, i.e., >98% conversion, for example, for 30 minutes at 80-85° C. After reaction is substantially complete, as determined by HPLC monitoring, the reaction mass was then cooled and quenched into water ((4 Vols) at (−)10 to 0° C. over a period of 3 to 5 hrs). The reaction mass was then cooled further and the temperature maintained for 2 hrs at −12 to 8° C. The mass was then filtered under nitrogen atmosphere to get the desired product 4-Chloro-3-formyl-benzenesulfonic acid (Stage-I), which may proceed to the next step (below) without drying and purification (Wet Wt: ~230 g, Purity by HPLC>95%).

Example-2

Synthesis of Benzaldehyde-2,5-Disulfonic Acid Sodium Salt

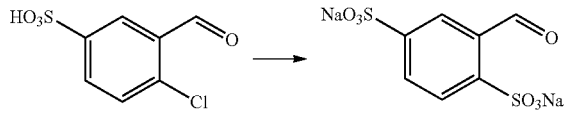

4-Chloro-3-formyl-benzenesulfonic acid (Stage-I) (Wet 230 g) was charged into purified water (0.65 Vol) and the mass pH adjusted from 2.5 to 11.0 with sodium hydroxide solution, with the combination maintained at 25-35° C. Sodium sulphite solution (99 g in 500 ml of Water) at 25-35° C. was then added over a period of 30 minutes. Reaction mass was then heated and maintained for sufficient time for substantial completion of the reaction, i.e., 12 hrs. at 100-102° C. After completion of reaction (monitored by HPLC), methanol (1.2 Lt) was added and the temperature reduced and maintained for 1 hr. at 25-35° C. The reaction mass was then heated and maintained for 1 hr. at 60-65° C., followed by cooling and maintaining the reaction for 1 hr at 25-35° C. The mass was then filtered and the resulting cake washed with methanol to obtain Benzaldehyde-2,5-disulfonic acid sodium salt (dry 160-170 g with >90% HPLC purity).

Example-3

Synthesis of 2-(Bis(4-diethylamino)phenyl)methyl)benzene-1,4-disulfonic Acid Disodium Salt

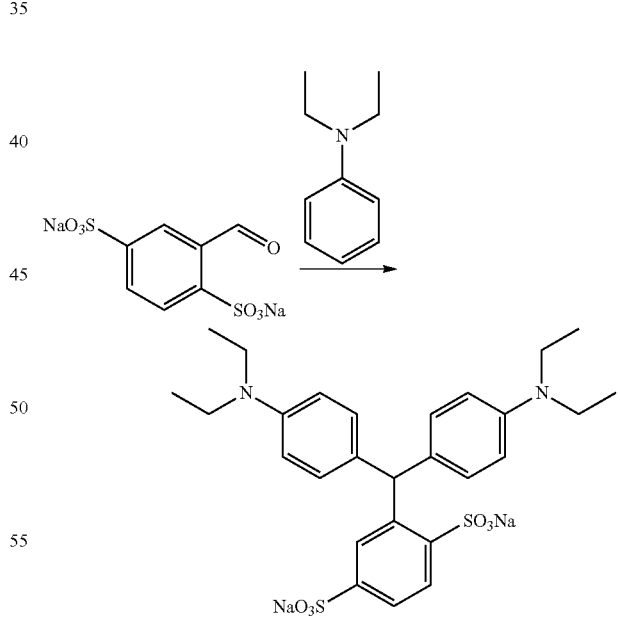

The benzaldehyde-2,5-disulfonic acid sodium salt (100 g, 0.322 mole, 1.0 eq) is mixed with acetic acid (6 Vols), urea (14.5 g, 0.241 mol, 0.75 eq), and then N,N-diethylaniline (96 g, 0.644 mol, 2.0 eq's) was added at 25-35° C. over a period of 60 minutes. The reaction mass was then heated and the temperature of the mass was maintained for sufficient time for substantial completion of the reaction, i.e., 25 hrs at 115-119° C. After completion of the reaction (monitored by HPLC), the mass was cooled and methanol (5 Vols) was added and maintained for 1 hr at 5-10° C. The compound was then filtered followed by washing with chilled purified water (2×75 ml), and the wet cake (~140 g) was dissolved into methanol (300 ml) and the pH of the mass adjusted to 10.5 to 11.5 with sodium hydroxide solution with the mass at 25-35° C. Undissolved particles were then filtered and the solvent of the filtrate is distilled off under vacuum to get the ISB crude. Isopropyl alcohol (200 ml) was added to the crude material and stirred for 30 minutes at 20-30° C. The mass of crude material was then filtered and washed with isopropyl alcohol (2×50 ml) to get the required 2-(Bis(4-diethylamino)phenyl)methyl) benzene-1,4-disulfonic acid disodium salt (dry 110-130 g, with HPLC>99.5%).

Example-4

Synthesis of Isosulfan Blue Crude Material

The 2-(Bis(4-diethylamino)phenyl)methyl) benzene-1,4-disulfonic acid disodium salt (100 g, 0.169 mol, 1.0 eq) was mixed with methanol (2.0 Lts), then Ammonium dichromate (23.5 g, 0.093 mol, 0.55 eq) was added and the mixture maintained for 30 minutes at 25-35° C. 125 g 40% W/W sulfuric acid solution at −10° C. to −4° C. was then added over a period of 60 minutes and the temperature maintained for substatnial completion of the reaction, i.e, 2 to 3 hrs. After completion of reaction (Monitored by HPLC), sodium carbonate (120 g) undissolved particles were filtered to get a filtrate and solid cake, and the solid cake was washed with methanol (2×200 ml). Filtrate was then taken and the solvent distilled off completely under vacuum to get the ISB material. Acetone (400 ml) was then charged onto the ISB material and maintained for 30 minutes at 45-50° C. Reaction mass was cooled and filtered to yield the desired ISB crude material (85-95 g with HPLC>90%).

Purification Procedure for Isosulfan Blue:

ISB crude material is then purified through flash chromatographic techniques using a dry loading method where the glass columns are replaced with pre-packed plastic cartridges containing silica gel, which are much safer and also more reproducible. Solvent is pumped through the cartridge, which is much quicker and more reproducible. It is useful for rapid, preparative separations with moderate resolution and is an alternative technique to preparative HPLC as it saves time and solvent.

Example-5

Purification of Isosulfan Blue.

The ISB crude material (5 g) was dissolved in methanol (50 ml) and silica gel (10 g) was added at 25-35° C. to the solution. The mixture was then agitated under vacuum until the solvent evaporates completely and only dry powder remains, preferably under vacuum and at below 50° C. The dry powder was taken and transferred into suitable sample loader which is connected to a "Biotage Sfar Silica-D-Duo 60 micro column". Later, the mobile phase containing 0.05% formic acid, DCM and methanol mixture (5% to 12% of Methanol in DCM) was run through the column by maintaining a flow rate at 50 ml per minute and a number of fractions were collected to get the pure Isosulfan blue. Major fractions having 98.02% purity and Desethyl Isosulfan blue (1.33%) along with other individual impurities and other decomposition products were observed in the mobile phase.

Example-6

Purification of Isosulfan Blue.

The ISB crude material (5 g) was dissolved in methanol (50 ml) and silica gel (10 g) was added to the solution. The mixture was agitated under vacuum until the solvent evaporated completely and only the dry powder remained, preferably under vacuum at below 50° C. Later, this dry powder was transferred into suitable sample loader which was connected to the "Biotage Sfar Silica-D-Duo 60 micro column". The mobile phase containing 0.05% Ammonia, DCM and methanol mixture (5% to 12% of Methanol in DCM) was run through the column by maintaining a flow rate of 50 ml per minute and a number of fractions collected to get the pure Isosulfan blue. The obtained major fractions had >99.8% purity and Desethyl Isosulfan Blue impurity (0.08%) with 35% yield.

Example-7

Purification of Isosulfan Blue.

The ISB crude material (5 g) material was dissolved in methanol (50 ml) and silica gel (10 g) was added to the solution at 25-35° C. The mixture was agitated under vacuum until the solvent evaporated completely and only the dry powder remained, preferably under vacuum at below 50° C. Later, this dry powder was transferred into a suitable sample loader which was connected to the "Biotage Sfar Silica-D-Duo 60 micro column". The mobile phase containing 0.05% Triethylamine (TEA), DCM and methanol mixture (5% to 12% of Methanol in DCM) was run through the column by maintaining a flow rate of 50 ml per minute and a number of fractions collected to get the pure Isosulfan blue. The obtained major fractions have >99.8% purity and Desethyl Isosulfan Blue impurity (0.09%) with 39% yield.

Example-8

Purification of Isosulfan Blue.

ISB crude material (10 g) was dissolved in methanol (100 ml) and silica gel (20 g) was added to the solution at 25-35° C. The mixture was agitated under vacuum until the solvent evaporated completely and only the dry powder remained, preferably under vacuum at below 50° C. Later, this dry powder was transferred into suitable sample loader which is connected to the "Biotage Sfar Silica-D-Duo 60 micro column". The mobile phase containing only Dichloromethane (MDC) and Methanol mixture with 92:8 ratio of MDC to methanol was run through the column by maintaining a flow rate 50 ml per minute and a number of fractions were collected to get the pure Isosulfan blue. All the fractions were collected, and the highly pure fractions were combined and the solvent distilled off to get the ISB material. Acetone was charged onto the ISB material, stirred for 60 minutes at 25-3° C. under nitrogen atmosphere. The desired mass was filtered, followed by washing with acetone (2×15 ml) to get pure Isosulfan blue. (Dry Wt: 6 g, yield: 60%; Purity: 99.85%, Desethyl Isosulfan blue impurity is within the pharmaceutical acceptable limits, as are also known and unknown impurities. The resultant product had the following characterization information:

$^1$H-NMR (DMSO/TMS): δ 1.18-1.21 (t, 12H, J=6.8 MHz), 3.59-3.64 (q, 8H, J=6.4 MHz), 6.96-6.98 (d, 4H, J=9.2 MHz), 7.143 (s, 1H), 7.27-7.29 (d, 4H, J=8.8 MHz), 7.74-7.76 (d, 1H, J=8.4 MHz), and 7.89-7.91 (d, 1H, J=8.0 MHz), $^{13}$C-NMR (DMSO/TMS): δ 13.19, 45.67, 113.56, 126.83, 127.02, 127.92, 128.04, 136.19, 140.58, 147.80, 148.11, 154.98 and 176.52.

ms: m/z. ~543.2 which corresponds to [M]$^+$.

In and embodiment, in order to utilize HPLC to detect the fractions from the column to be combined to get the substantially pure ISB, various procedures are carried out, as more specifically identified below.

Analytical Method

1. Related Substances by HPLC, % w/w:

Reagents & Chemicals:
  Di-Potassium hydrogen phosphate (AR Grade or Equivalent)
  Orthophosphoric acid (85%) (AR Grade or Equivalent)
  Acetonitrile (HPLC Grade)
  Water (Milli-Q)

Standards:
Isosulfan Blue (7525)
  2-(Bis(4-diethylamino)phenyl)methyl)benzene-1,4-disulfonic acid disodium salt (5870)
Desethyl Isosulfan Blue Impurity Preparation of Diluted Ortho Phosphoric Acid Solution:
  Dilute 1.0 mL of ortho phosphoric acid to 100 mL with water.

Preparation of Mobile Phase-A:
  Take 1000 mL Milli-Q water into a 2 liter beaker, to this add about 4.36 g [0.025M] of Di-Potassium hydrogen phosphate, sonicate to dissolve and adjust the pH to 7.2±0.05 with diluted Orthophosphoric acid. Filter through 0.45 μm-membrane and degas.

Preparation of Mobile Phase-B:
  Take 250 mL Mobile phase-A and 750 mL of Acetonitrile into a 2 liter beaker, Filter through 0.45 μm-membrane and degas.
  Note-1: Mobile phase is stable up to 3 days at room temperature.

Chromatographic Conditions:
  The Liquid chromatography equipped with variable UV detector and following parameters
  Column: X-TERRA RP 8,150×4.6 mm, 3.5 μm (Make—Waters or equivalent).
  Wave length: 220 nm.
  Flow rate: 1.0 mL/min.
  Column Temp: 25° C.
  Injection volume: 10 μL
  Run time: 40 min.
  Diluent: Water Gradient Programme:

| Time (minutes) | Mobile Phase-A | Mobile Phase-B |
|---|---|---|
| Initial | 73 | 27 |
| 10 | 73 | 27 |
| 21 | 0 | 100 |
| 31 | 0 | 100 |
| 32 | 73 | 27 |
| 40 | 73 | 27 |

Preparation of System Suitability Solution:
(Solution is Stable Up to 5 Days when Stored at 2-8° C.)
  Weigh accurately about each 10 mg of 2-(Bis(4-diethylamino)phenyl)methyl) benzene-1,4-disulfonic acid disodium salt (5870) standard and Isosulfan Blue (7525) into a 25 mL volumetric flask and add 7.0 mL of diluent, sonicate to dissolve, make up to the mark with diluent.

Preparation of Standard Solution (0.15% Solution):
(Solution is Stable Up to 5 Days when Stored at 2-8° C. & Bench Top)
  Weigh accurately 15 mg of Desethyl isosulfan blue impurity and 15 mg of Isosulfan Blue (7525) standard into a 100 mL volumetric flask and add 70 mL of diluent, sonicate to dissolve, make up to the mark with diluent.
  Take 1 mL of above solution into 100 mL volumetric flask dissolve, make up to the mark with diluent.

Preparation of Sample Solution:
(Solution is Stable Up to 5 Days when Stored at 2-8° C. & Bench Top).
  Weigh accurately 10 mg of sample into a 10 mL volumetric flask and add 2.0 mL of diluent, sonicate to dissolve, make up to the mark with diluent.

Procedure:
  Equilibrate the HPLC instrument at least 30 minutes under specified method conditions. Inject one or more blank injections, Inject system suitability solution one injection and inject standard solution six Injections. The system is suitable if and only if:
  Resolution between Isosulfan blue (7525) and 2-(Bis(4-diethylamino)phenyl)methyl) benzene-1,4-disulfonic acid disodium salt (5870) peak from system suitability solution should be not less than 5.0.
  Resolution between Desethyl isosulfan blue and Isosulfan blue (7525) peak from first injection of standard solution should be not less than 5.0
  Theoretical plates for Isosulfan blue (7525) peak from first injection of standard solution should be not less than 3000.
  The % RSD for the peak area response of Isosulfan blue (7525) and Desethyl isosulfan blue from six replicate injections of standard solution should be not more than 10.0
  If system suitability criteria met inject sample solution one injection. Inject Bracketing standard at the end of the each sequence or after every six sample injections.
  The % RSD for the peak area response of Isosulfan blue (7525) and Desethyl isosulfan blue from standard solution with bracketing standard should be not more than 10.0.
  Record the peak area response and disregard the peaks due to diluent.

Retention time table RT, RRT, RRF, LOD & LOQ table:

| Name of the Compound | Retention time minutes (Approx) | RRT | RRF | LOD % | LOQ % |
|---|---|---|---|---|---|
| Desethyl Isosulfan Blue | 5.9 | 0.54 | 0.77 | 0.0057 | 0.0115 |
| Isosulfan Blue (7525) | 10.8 | 1.00 | 1.00 | 0.0113 | 0.0212 |
| 2-(Bis(4-diethylamino)phenyl)methyl)benzene-1,4-disulfonic acid disodium salt (5870) | 16.2 | 1.50 | 1.00 | NA | NA |

Note:
Consider 5870 peak as an unspecified impurity. LOD & LOQ values of 7525 peak is applicable.

Calculation:

Desethyl isosulfan blue impurity, $$\% \ w/w := \frac{A_{SMP1}}{A_{STD1}} \times \frac{W_{STD1}}{V_{STD}} \times \frac{1}{100} \times \frac{V_{SMP}}{W_{SMP}} \times P.$$

Where,
- $A_{SMP1}$=Area of Desethyl isosulfan blue area from sample solution
- $A_{STD1}$=Avg Area of Desethyl isosulfan blue area from standard solution
- $W_{STD1}$=Weight of Desethyl isosulfan blue standard (in mg)
- $V_{STD}$=Desethyl isosulfan blue standard diluted Volume (in mL)
- $V_{SMP}$=Sample diluted volume (in mL)
- $W_{SMP}$=Weight of Sample (in mg)
- P=Purity of Desethyl isosulfan blue standard For all other individual impurity, $$\% \ w/w := \frac{A_{SMP2}}{A_{STD2}} \times \frac{W_{STD2}}{V_{STD}} \times \frac{1}{100} \times \frac{V_{SMP}}{W_{SMP}} \times P.$$

Where,
- $A_{SMP2}$=Area of individual impurity area from sample solution
- $A_{STD2}$=Avg Area of isosulfan blue area from standard solution
- $W_{STD2}$=Weight of isosulfan blue standard (in mg)
- $V_{STD}$=Isosulfan blue standard diluted Volume (in mL)
- $V_{SMP}$=Sample diluted volume (in mL)
- $W_{SMP}$=Weight of Sample (in mg)
- P=Purity/Potency of Isosulfan blue standard Total Impurities:
=% Desethyl isosulfan blue impurity+ all other individual impurities.

Note: For total impurities calculation, consider the impurities which are above LOQ value.

A chromatogram for a blank is shown at FIG. 2. This is done to establish a baseline criteria for the instrument to remove noise.

A chromatogram of System suitability for ISB is shown at FIG. 3. This basically shows a chromatogram of ISB to be the reference for ISB for the system being used.

Isosulfan Blue—Specifications for Validation Batches Results (Shown Below at Table 1)

TABLE 1

FINSIHED PRODUCT TEST RESULTS

| S. No. | Test | Specification | Test results of validation Batches | | |
|---|---|---|---|---|---|
| | | | 7525/21/3008 | 7525/21/3009 | 7525/21/3010 |
| 1. | Appearance | Green to dark purple powder | Green powder | Green powder | Green powder |
| 2. | Appearance of solution (10 mg/ml in water) | Clear dark blue solution | Clear dark blue solution | Clear dark blue solution | Clear dark blue solution |
| 3. | Identity (FT-IR) | Conforms to reference | Conforms to reference | Conforms to reference | Conforms to reference |
| 4. | Identity (HPLC) | The retention time of the major peak obtained from sample preparation should match with standard retention time from assay by HPLC | The retention time of major peak obtained from sample preparation is matched with standard retention time from Assay by HPLC. | The retention time of major peak obtained from sample preparation is matched with standard retention time from Assay by HPLC. | The retention time of major peak obtained from sample preparation is matched with standard retention time from Assay by HPLC. |
| 5. | Water content by KF, % w/w | Not more than 11 | 8.3 | 5.3 | 5.0 |
| 6. | pH (1% in $H_2O$) | 6.0-8.5 | 7.34 | 7.30 | 7.32 |
| 7. | Chromium by ICP, ppm | Not more than 100 | BQL (i.e.25) | BQL (i.e.25) | BQL (i.e.25) |
| 8. | | Related substances by HPLC, % w/w | | | |
| | Desethyl isosulfan Blue | Not more than 0.30 | 0.05 | 0.04 | 0.05 |
| | Impurity at RRT 0.20 | Not more than 0.15 | 0.01 | 0.01 | 0.01 |
| | Any unspecified impurity | Not more than 0.10 | 0.09 | 0.03 | 0.04 |
| | Total impurities | Not more than 1.0 | 0.18 | 0.08 | 0.08 |
| 9. | Assay by HPLC, % w/w (on anhydrous basis) | Between 98.0 and 102.0 | 100.6 | 101.3 | 101.3 |
| 10. | Total aerobic microbial content (TAMC) | Not more than 1000 cfu/g | <10 | <10 | <10 |
| 11. | Bacterial endotoxins (BET) | Not more than 5 EU/mg | <5 | <5 | <5 |
| 12. | | Residual solvents by GC, PPM | | | |
| | a) Methanol | Not more than 3000 | 63 | 288 | 254 |
| | b) Isopropyl alcohol | Not more than 5000 | None Detected | None Detected | None Detected |
| | c) Dichloromethane | Not more than 500 | None Detected | 32 | 36 |
| | d) Acetone | Not more than 5000 | 626 | 286 | 292 |

TABLE 1-continued

FINSIHED PRODUCT TEST RESULTS

| S. No. | Test | Specification | Test results of validation Batches | | |
|---|---|---|---|---|---|
| | | | 7525/21/3008 | 7525/21/3009 | 7525/21/3010 |
| 13. | Acetic acid content by HPLC, ppm | Not more than 5000 | 187 | 253 | 178 |

Elemental analysis Data is shown below at Table 2: JSB material after final purification.

TABLE 2

Elemental Impurities risk assessment summary results of Isosulfan Blue

| S.No. | Elemental impurity | Class | Specification (ppm) (As per ICH Q3D & USP <232>) | Control Threshold Limit (ppm) | LOQ (25% Specification level) (ppm) | Results (ppm) | | |
|---|---|---|---|---|---|---|---|---|
| | | | | | | 7525/21/3008 | 7525/21/3009 | 7525/21/3010 |
| 1. | Cadmium (Cd) | 1 | 0.5 | 0.150 | 0.050 | 0.026 | 0.025 | 0.024 |
| 2 | Lead (Pb) | | 0.5 | 0.150 | 0.125 | 0.101 | 0.096 | 0.100 |
| 3. | Arsenic (As) | | 1.5 | 0.460 | 0.375 | 0.026 | 0.024 | 0.024 |
| 4. | Mercury (Hg) | | 3 | 0.900 | 0.075 | 0.025 | 0.024 | 0.024 |
| 5. | Cobalt (Co) | 2A | 5 | 1.500 | 0.125 | 0.011 | 0.010 | 0.010 |
| 6 | Vanadium (V) | | 10 | 3.000 | 0.250 | 0.026 | 0.024 | 0.024 |
| 7. | Nickel (Ni) | | 20 | 6.000 | 0.500 | 0.255 | 0.246 | 0.236 |
| 8. | Thallium (Tl) | 2B | 0.8 | 0.240 | 0.200 | 0.000 | 0.000 | 0.000 |
| 9. | Gold (Au) | | 10 | 3.000 | 2.500 | 0.137 | 0.140 | 0.128 |
| 10. | Palladium (Pd) | | 10 | 3.000 | 0.250 | 0.196 | 0.184 | 0.181 |
| 11 | Iridium (Ir) | | 10 | 3.000 | 0.250 | 0.000 | 0.000 | 0.000 |
| 12. | Osmium (Os) | | 10 | 3.000 | 0.250 | 0.049 | 0.052 | 0.050 |
| 13 | Rhodium (Rh) | | 10 | 3.000 | 0.250 | 0.000 | 0.000 | 0.000 |
| 14. | Ruthenium (Ru) | | 10 | 3.000 | 0.250 | 0.000 | 0.000 | 0.000 |
| 15. | Selenium (Se) | | 15 | 4.500 | 2.000 | 0.058 | 0.042 | 0.046 |
| 16. | Silver (Ag) | | 15 | 4.500 | 0.250 | 0.050 | 0.047 | 0.047 |
| 17 | Platinum (Pt) | | 10 | 3.000 | 0.250 | 0.000 | 0.000 | 0.000 |
| 18. | Lithium (Li) | 3 | 55 | 16.500 | 6.250 | 0.450 | 0.440 | 0.460 |
| 19. | Antimony (Sb) | | 120 | 36.000 | 2.250 | 0.025 | 0.025 | 0.026 |
| 20. | Barium (Ba) | | 140 | 42.000 | 17.500 | 0.407 | 0.381 | 0.358 |
| 21. | Molybdenum (Mo) | | 300 | 90.000 | 37.500 | 0.093 | 0.068 | 0.045 |
| 22. | Copper (Cu) | | 300 | 90.000 | 7.500 | 1.238 | 1.100 | 1.107 |
| 23. | Tin (Sn) | | 600 | 180.000 | 16.000 | 0.122 | 0.111 | 0.095 |
| 24. | Chromium (Cr) | | 1100 | 330.000 | 27.500 | 1.253 | 1.230 | 1.230 |

In an embodiment, analytical methods include obtaining information on different compounds exiting a column, and some of the information is shown at FIGS. 4A and 4B. FIG. 4A is a chromatogram of LOQ (limit of quantification) Standard Chromatogram, which shows the limit of quantification for ISB with impurities. FIG. 4B shows a chromatogram of Standard Sample (ISB) Chromatogram, which is also a test of impurity and ISB in a sample. FIG. 5 shows a testing of diluent.

Information for specific samples is in the Figures. A chromatogram of a standard solution is shown at FIG. 6, which is a test of purified ISB. Test results of an actual sample is found at FIG. 7, which shows the high degree of purity of ISB and the low amount of impurities.

The Isosulfan blue synthesis and purification process with flash chromatography technique according to the present invention is simple, fast, cost effective and results in better quality than other methods and provides pharmaceutical acceptable limits of known and unknown impurities.

The invention claimed is:

1. A composition comprising a N-[4-[[4-(diethyl amino) phenyl](2,5-disulfophenyl)methylene]-2,5-cyclohexadien-1-ylidene]-N-ethylethanaminium sodium salt and a desethyl isosulfan blue impurity, wherein the N-4-4-(diethylamino) phenyl (2,5-disulfophenyl)methylene-2,5-cyclohexadien-1-ylidene-N-ethylethanaminium sodium salt is at least 90% of the weight of such composition and wherein the desethyl isosulfan blue impurity is less than 0.07% by weight.

2. The composition according to claim 1, wherein the N-4-4-(diethylamino)phenyl (2,5-disulfophenyl)methylene-2,5-cyclohexadien-1-ylidene-N-ethylethanaminium sodium salt is 90% to 99.9% of the weight of such composition.

3. The composition according to claim 1, wherein the N-4-4-(diethylamino)phenyl (2,5-disulfophenyl)methylene-2,5-cyclohexadien-1-ylidene-N-ethylethanaminium sodium salt is 99.0% to 99.9% of the weight of such composition.

4. The composition according to claim 1, wherein the composition comprises 2-(Bis(4-diethylamino)phenyl) methyl)benzene-1,4-disulfonic acid disodium salt, and wherein such 2-(Bis(4-diethylamino)phenyl)methyl)benzene-1,4-disulfonic acid disodium salt is not more than 0.1% of the weight of the composition.

5. The composition according to claim 1, wherein the composition comprises the following impurities: arsenic, lead, mercury, cadmium, cobalt, vanadium, and nickel, wherein an amount of arsenic is by weight below 0.030 ppm, an amount of lead is by weight below 0.110 ppm, an amount of mercury is by weight below 0.03 ppm, an amount of cadmium is by weight below 0.030 ppm, an amount of cobalt is by weight below 0.015 ppm, an amount of vanadium is by weight below 0.030 ppm, and an amount of nickel is by weight below 0.300 ppm.

6. The composition according to claim 1, wherein the composition comprises a chromium impurity, and wherein an amount of chromium is not more than 1.3 ppm by weight.

7. A substantially pure N-[4-[[4-(diethyl amino) phenyl](2,5-disulfophenyl)methylene]-2,5-cyclohexadien-1-ylidene]-N-ethylethanaminium sodium salt having a desethyl isosulfan blue impurity and wherein the desethyl isosulfan blue impurity is less than 0.07% by weight made by a process comprising the steps of:
  a sulphonating step comprising sulphonating 2-chlorobenzaldehyde with a sulphonating agent to obtain 4-chloro-3-formyl sulphonic acid;
  a treatment step comprising treating 4-chloro-3-formyl sulphonic acid with sodium sulphite and subsequent basification thereof to obtain 1-formyl benzene-2,5-sulphonic acid disodium salt;
  a condensation step comprising condensation reacting of 1-formyl benzene-2,5-sulphonic acid disodium salt with N,N-diethylaniline using a first acid to obtain a 4-[Bis[4-diethylamino)phenyl]methyl]benzene-2,5-disulphonic acid disodium salt;
  wherein the condensation step further comprises adjusting the pH with sodium hydroxide;
  an oxidation step comprising oxidation reacting of 4-[bis[4-(diethylamino)phenyl]methyl]benzene-2,5-disulphonic acid disodium salt with an oxidizing agent, using a second acid and a solvent, to obtain N-4-4-(diethylamino)phenyl (2,5-disulfophenyl)methylene-2,5-cyclohexadien-1-ylidene-N-ethylethanaminium sodium salt;
  a purification step comprising purification of N-4-4-(diethylamino)phenyl (2,5-disulfophenyl)methylene-2,5-cyclohexadien-1-ylidene-N-ethylethanaminium sodium salt; and
  utilizing HPLC to monitor the sulphonating step, the treatment step, the condensation step, and/or the oxidation step, to determine when one or more reactions of such sulphonating step, treatment step, condensation step, and/or oxidation step are substantially complete and ending such one or more reactions on the basis of the HPLC monitoring.

8. The substantially pure N-4-4-(diethylamino)phenyl (2,5-disulfophenyl)methylene-2,5-cyclohexadien-1-ylidene-N-ethylethanaminium sodium salt according to claim 7, wherein:
  the sulphonating agent in the sulphonating step comprises oleum;
  the basification of the treatment step comprises the use of NaOH solution;
  the first acid in the condensation step comprises acetic acid or hydrochloric acid; and
  the second acid and the solvent of the oxidation step comprise sulfuric acid and methanol, respectively.

9. The substantially pure N-4-4-(diethylamino)phenyl (2,5-disulfophenyl)methylene-2,5-cyclohexadien-1-ylidene-N-ethylethanaminium sodium salt according to claim 7, wherein:
  the sulphonating agent in the sulphonating step comprises the oleum having a concentration of 15-30%;
  the basification of the treatment step comprises adjusting the pH to 10-11.5;
  the treatment step further comprises isolation to obtain solid 1-formyl benzene-2,5-sulphonic acid disodium salt;
  wherein the condensation step further comprises adjusting the pH to 10.5 to 11.5 with the sodium hydroxide in the presence of methanol and isolating; and
  wherein the oxidation step is carried out at −10 to −4 degrees Celsius, and wherein the N-4-4-(diethylamino) phenyl (2,5-disulfophenyl)methylene-2,5-cyclohexadien-1-ylidene-N-ethylethanaminium sodium salt is isolated.

10. The substantially pure N-4-4-(diethylamino)phenyl (2,5-disulfophenyl)methylene-2,5-cyclohexadien-1-ylidene-N-ethylethanaminium sodium salt according to claim 7, wherein the purification step comprises the use of flash chromatography.

11. The substantially pure N-4-4-(diethylamino)phenyl (2,5-disulfophenyl)methylene-2,5-cyclohexadien-1-ylidene-N-ethylethanaminium sodium salt according to claim 7, wherein the purification step comprises the use of flash chromatography with 5-10% of methanol in a methylene chloride mixture, and wherein the purification step further comprises mixing fractions from the flash chromatography, distilling solvent, and washing with acetone to obtain the substantially pure N-4-4-(diethylamino)phenyl (2,5-disulfophenyl)methylene-2,5-cyclohexadien-1-ylidene-N-ethylethanaminium sodium salt.

12. The substantially pure N-4-4-(diethylamino)phenyl (2,5-disulfophenyl)methylene-2,5-cyclohexadien-1-ylidene-N-ethylethanaminium sodium salt according to claim 7, wherein HPLC is used to monitor the sulphonating step, the treatment step, the condensation step, and the oxidation step to determine when one or more reactions of such sulphonating step, treatment step, condensation step, and oxidation step are substantially complete and ending such one or more reactions on the basis of the HPLC monitoring.

\* \* \* \* \*